United States Patent [19]

Brown et al.

[11] 4,145,913

[45] Mar. 27, 1979

[54] GAS DETECTORS

[75] Inventors: Cyril Brown, Gerrards Cross; Christopher J. Derrett, London, both of England

[73] Assignee: National Research Development Corporation, London, England

[21] Appl. No.: 771,981

[22] Filed: Feb. 25, 1977

[30] Foreign Application Priority Data

Mar. 1, 1976 [GB] United Kingdom ............... 08076/76

[51] Int. Cl.$^2$ ...................... G01N 27/42; G01N 31/06
[52] U.S. Cl. ...................................... 73/23; 324/30 B
[58] Field of Search .................. 73/23, 23.1; 324/30 B

[56] References Cited

U.S. PATENT DOCUMENTS

| | | | |
|---|---|---|---|
| 2,897,436 | 7/1959 | Douty | 324/30 B |
| 2,902,639 | 9/1959 | Thayer et al. | 324/30 B |
| 3,674,672 | 7/1972 | Whitesell | 324/30 B |
| 3,916,300 | 10/1975 | Chisdes et al. | 324/30 B |
| 3,934,193 | 1/1976 | Hall | 324/30 B |
| 3,965,414 | 6/1976 | Teass | 324/30 B |

FOREIGN PATENT DOCUMENTS 1014561 12/1965 United Kingdom ........................ 73/23

*Primary Examiner*—Stephen A. Kreitman
*Attorney, Agent, or Firm*—Cushman, Darby & Cushman

[57] ABSTRACT

Apparatus for determining the concentration of a component of a gaseous mixture by selective absorption of the component in a liquid absorbent and measurement of a property of the absorbent, such as the electrical conductivity, related to the concentration of the component therein, comprising an absorption cell for containing the liquid absorbent; means for bringing a stream of said gaseous mixture into contact with the absorbent; means for flushing the absorption cell with absorbent from a reservoir so as to recharge the cell with absorbent; and means for providing a first signal related to said property of the absorbent immediately after flushing the cell, for providing a second signal related to the property after a predetermined time, and for providing a third signal related to the difference between the second and first signals.

5 Claims, 4 Drawing Figures

GAS DETECTORS

This invention relates to gas detectors, particularly detectors for determining the concentration of small quantities of a gas or vapour in a mixture with a 'neutral gas' such as sulphur dioxide in atmospheric air.

In British Pat. No. 1,014,561 there is disclosed apparatus for measuring the concentration of sulphur dioxide in air using a conductivity cell which is flushed with fresh reagent at about 20 minute intervals. The conductivity change is calculated by reading two points on a chart recorder, which is tedious if longterm monitoring is required. The present invention is intended to overcome this disadvantage.

The 'neutral gas' referred to above is a gas which does not dissolve in the reagent or with which the reagent is already saturated.

According to the invention, there is provided an apparatus for determining the concentration of a component of a gaseous mixture by selective absorption of the component in a liquid absorbent and measurement of a property of the absorbent related to the concentration of the component therein, the apparatus comprising an absorption cell for containing the liquid absorbent; means for bringing a stream of said gaseous mixture into contact with the absorbent; means for flushing the absorbent cell with absorbent from a reservoir so as to recharge the cell with absorbent; and means for providing a first signal related to said property of the absorbent immediately after flushing the cell, for providing a second signal related to the property after a predetermined time, and for providing a third signal related to the difference between the second and first signals.

Preferably the apparatus further comprises means for returning the absorbent flushed from the cell to the reservoir.

Preferably the apparatus is cyclically operable and the second signal is provided immediately before flushing the cell at the beginning of the next cycle of operation.

In one arrangement the means for bringing a stream of the gaseous mixture into contact with the absorbent comprises a jet-forming means arranged to direct a jet of the gaseous mixture on to the surface of the absorbent.

Said property of the absorbent will usually by the electrical conductivity, which may be measured by means of two electrodes positioned in the absorption cell, but may also be an optical property, in which case at least part of the wall of the absorption cell is made of a transparent material.

In one embodiment of the apparatus there is provided temperature sensitive means arranged to compensate the first and second signals in accordance with the temperature of the absorption cell.

The invention will now be described by way of example with reference to the accompanying drawings in which.

Figure 1:
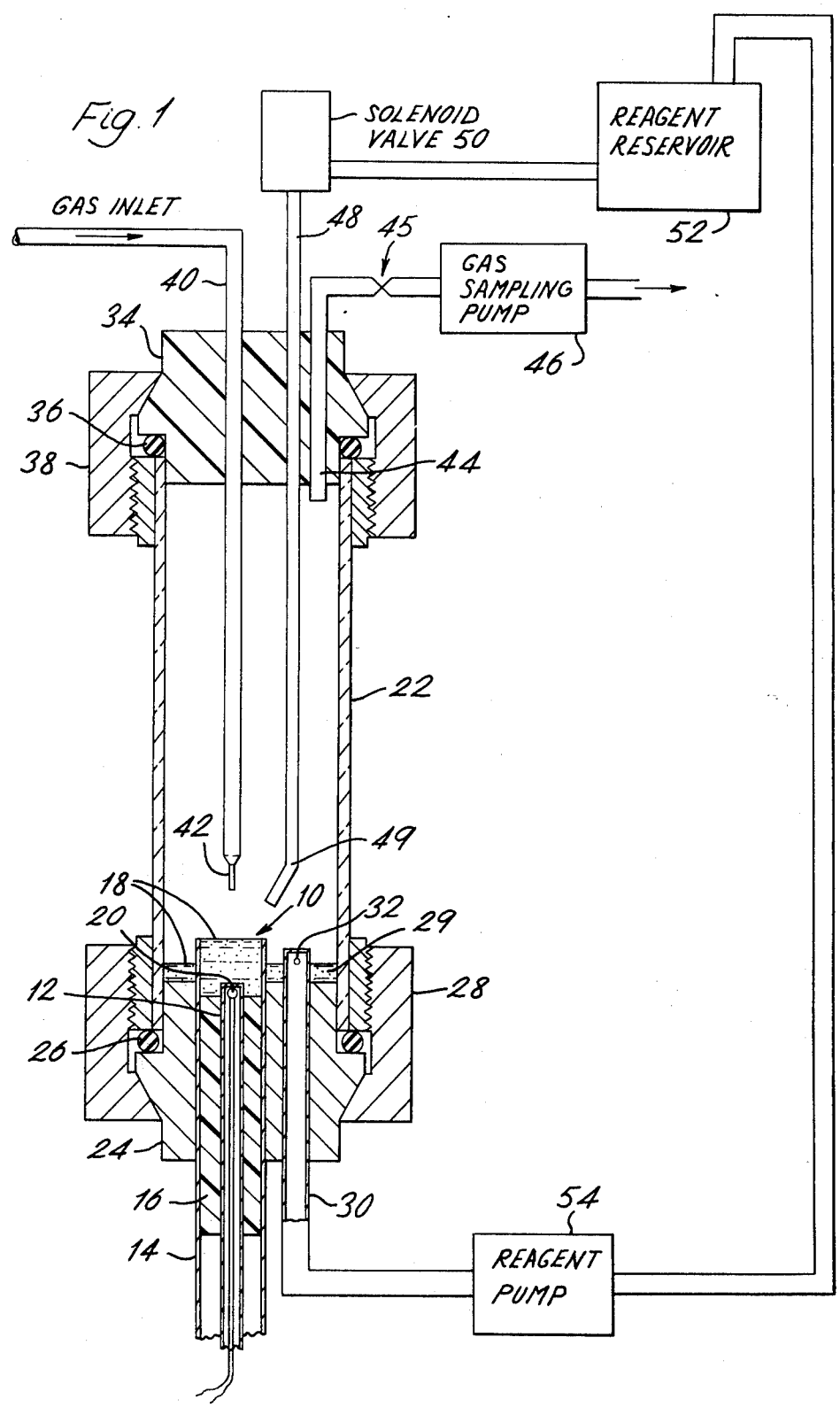
FIG. 1 illustrates in section apparatus for measuring the concentration of a gas in atmospheric air.

In FIG. 1 a conductivity cell indicated generally by reference 10 consists of an inner stainless steel tube 12 having a closed end and an outer open-ended stainless steel tube 14, arranged concentrically and spaced from each other by a polyethylene tube 16 which forms a liquid-tight seal. The outer tube projects beyond the inner tube and polyethylene tube to form a container for a liquid reagent 18. The inner tube 12 projects slightly beyond the polyethylene tube so that its closed end is immersed in the reagent, and a thermistor 20 is arranged inside the inner tube.

The conductivity cell 10 is supported at the lower end of a vertical, wide-bore glass tube 22 by a stainless steel insert 24, which has an 'O' ring seal 26 and is held by a screw cap 28 which screws on to the tube 22. The cell 10 is arranged with its lower half surrounded by reagent 29 which acts as a heat sink, and its upper half projecting above the reagent. The insert 24 also supports a drainage tube 30 having a drainage port 32 above the upper face of the insert and below the top of the cell 10.

The upper end of the glass tube 22 has a similar insert 34, 'O' ring 36, and screw cap 38, supporting three tubes:

a gas inlet tube 40 which terminates in a hypodermic needle forming an impinger jet 42 arranged slightly off-centre above the conductivity cell 10;

a gas extraction tube 44 connected through a critical orifice 45, in the form of a stainless steel capillary tube and which controls the flow rate, to a gas sampling pump 46; and a flushing tube 48 connected through a solenoid valve 50 having a body of polyethylenetetrafluoride to a reagent reservoir 52.

The lower end 49 of the flushing tube 48 is positioned just above the conductivity cell 10. The drainage tube 30 is connected through a reagent pump 54 and return tube 56 to an inlet at the top of the reservoir.

In use, the sampling pump 46 operates continuously to draw atmospheric air through the gas inlet tube 40 and through the impinger jet 42 so that a jet of air impinges on the surface of the reagent 18. The rate of flow is chosen so that a small dimple forms on the reagent surface.

If the reagent is acidified hydrogen peroxide (0.2 volume hydrogen peroxide and $3 \times 10^{-5}$N sulphuric acid) and the atmospheric air contains sulphur dioxide, the sulphur dioxide will combine with the reagent to form sulphuric acid and cause the electrical conductivity of the reagent to increase in proportion to the concentration of dissolved gas.

When the solenoid valve 50 is opened to allow reagent from the reservoir to pass down the flushing tube 48, the apparatus is arranged so that the fresh reagent flows under the gravity fast enough to completely flush the used reagent from the conductivity cell and replace it. The flushed reagent floods into the lower part of the glass tube 22 and most of it is pumped away through the drainage port 32 by the reagent pump 54 and returned to the reservoir. The upper end of the outer tube 14 provides a well-defined edge at which a meniscus forms so that the volume of reagent in the cell varies very little from cycle to cycle. The volume is typically 0.5 milliliter.

Figure 2:
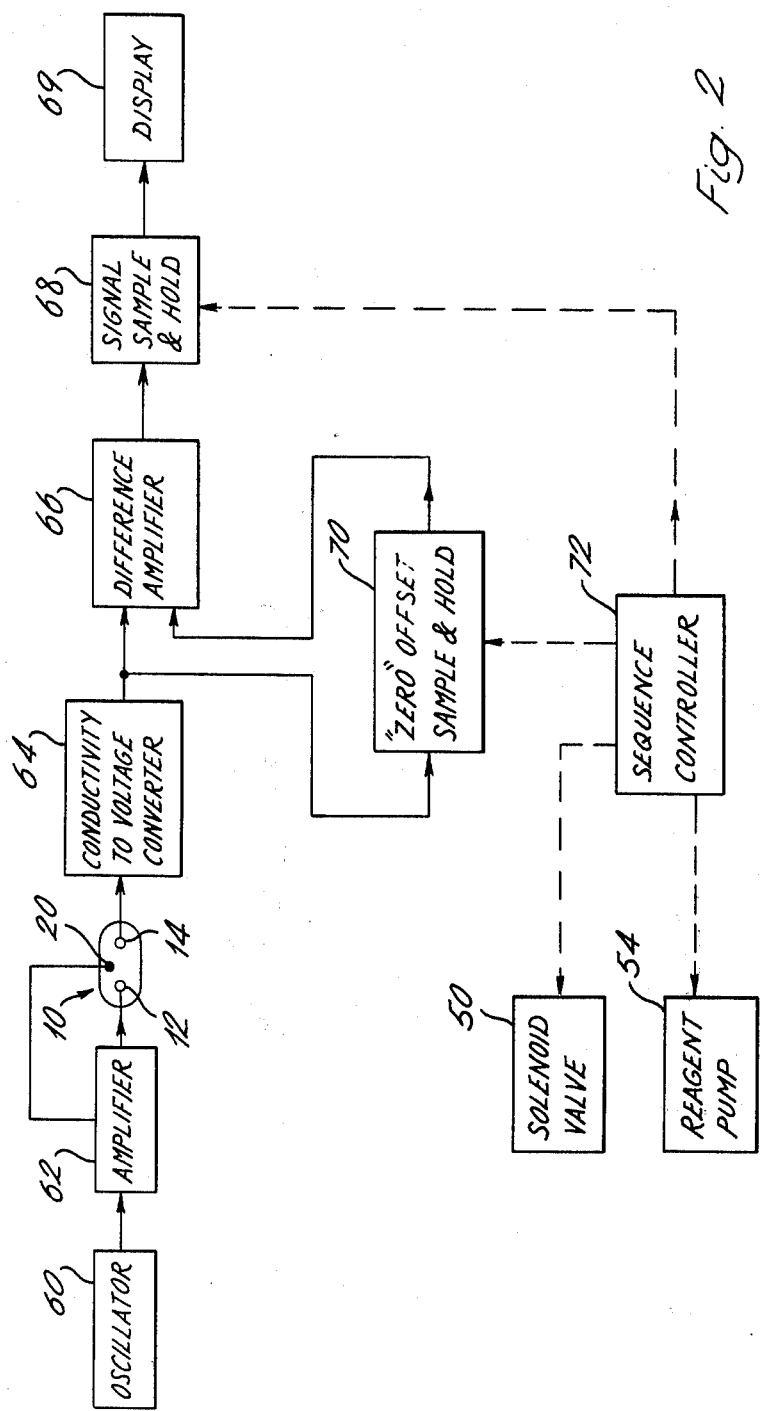
FIG. 2 is a schematic diagram of the electrical circuit associated with the apparatus shown in FIG. 1.

The apparatus shown in FIG. 1 is controlled by the electrical circuit shown in FIG. 2. In the conductivity cell 10, the inner and outer stainless steel tubes 12, 14 act as electrodes. An oscillator 60 is connected through an amplifier 62 to one electrode 12, and the other electrode 14 is connected to a high-impedance amplifier 64 which acts as a conductivity-to-voltage converter. The amplifier 64 supplies one input of a difference amplifier 66 which is connected through a signal sample and hold unit 68 to a display unit 69. The other input is supplied by a zero offset and hold unit 70 also connected to amplifier 64 and operated by a sequence controller 72 which also controls the sample and hold unit 68, the solenoid valve 50, and the reagent pump 54. The thermistor 20 in the conductivity cell is connected to the amplifier 62 to alter the amplification in accordance with variations in the temperature of the conductivity cell 10, caused, for example, by evaporative cooling by the air jet.

Figure 3:
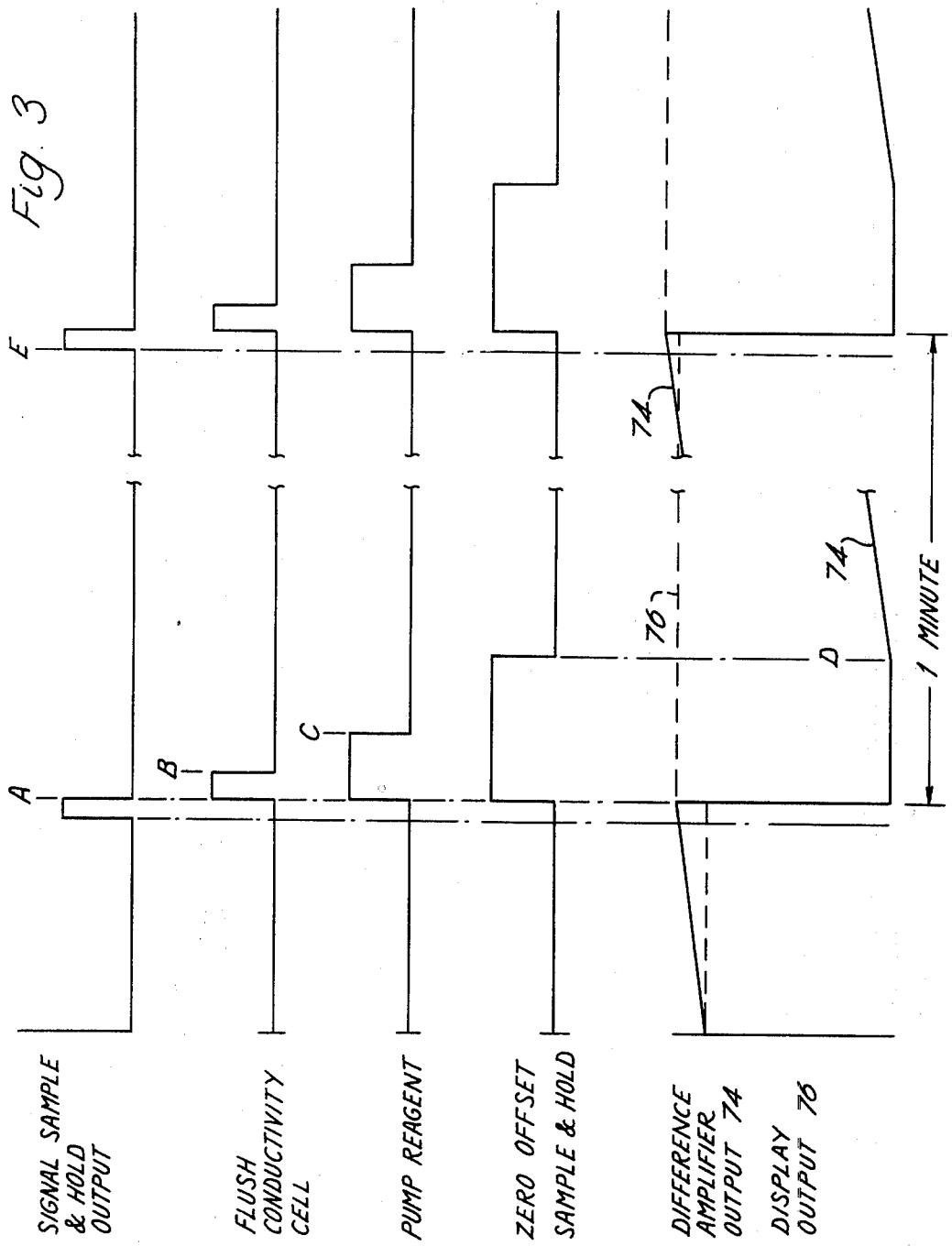
FIG. 3 illustrates the sequence of operation of the parts of the apparatus.

The sequence of operations is controlled by the sequence controller 72, and is shown in FIG. 3.

At the beginning of a cycle, at time A, the solenoid valve 50 is opened to flush the conductivity cell, and simultaneously the reagent pump 54 starts to operate. At time B the solenoid valve closes so that no further reagent is supplied, and shortly afterwards at time C the reagent pump stops pumping. At time D the zero offset sample and hold unit 70 operates by storing the output signal from amplifier 54 which corresponds to the conductivity of the cell at that time. The stored signal is supplied to one input of the difference amplifier 66 during the period D to E. The next cycle then starts.

As the freshly-supplied reagent in the cell is exposed to the jet of air containing sulphur dioxide, the conductivity increases; the output of the amplifier 64 therefore increases and is supplied to the second input of the difference amplifier 66. The output of amplifier 66 corresponds to the increase in concentration of sulphur dioxide in the reagent during this cycle, and also slowly increases with time as shown by the full line 74 (FIG. 3). However the sequence controller 72 controls the signal sample and hold unit 68 so that the signal from the difference amplifier 66 is accepted only during the period D to E immediately before the start of the next cycle. The hold unit 68 supplies this voltage signal to the display unit 69 at the end of the cycle, cancelling the previous display. The display unit 69 provides a display in accordance with the new signal; the quantity displayed at any time is therefore the mean $SO_2$ concentration detected during the period D to E of the previous cycle, and is indicated in FIG. 3 by the chain-dotted line 76.

Figure 4:
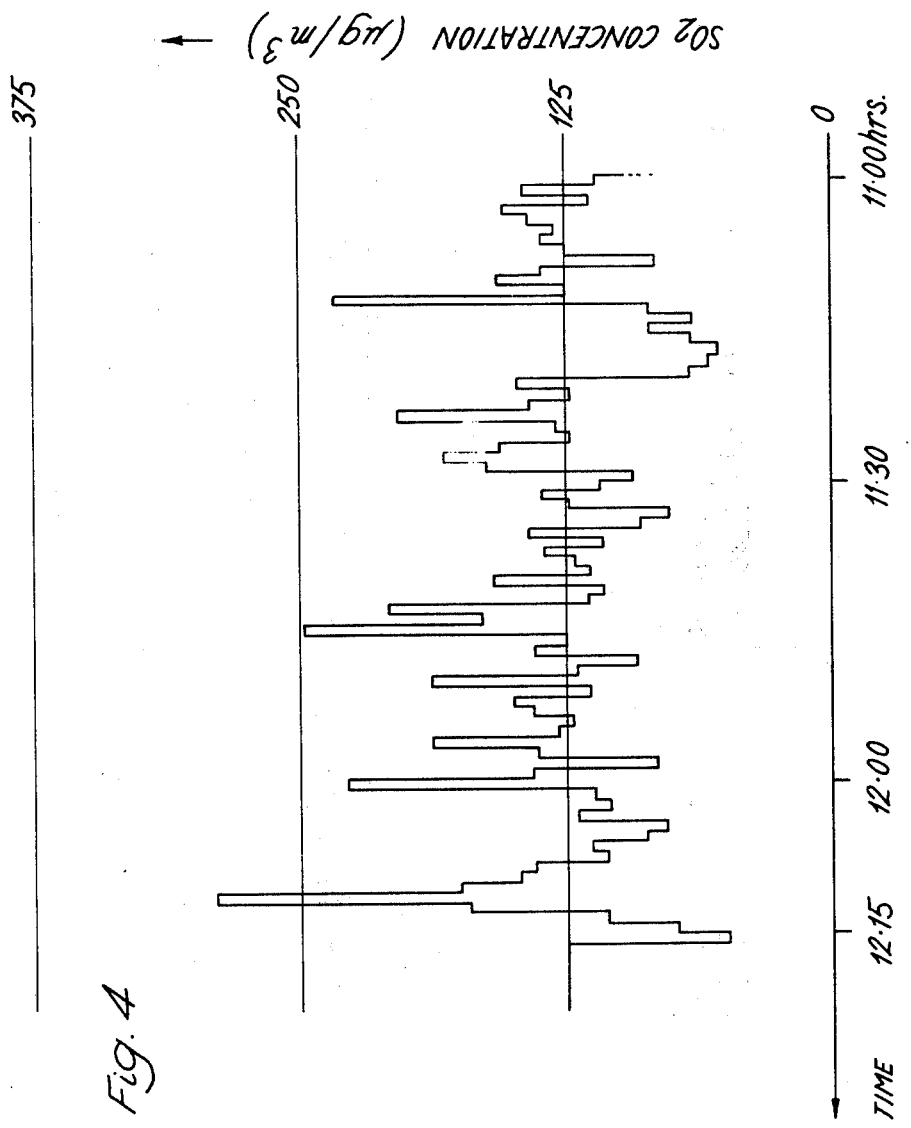
FIG. 4 is a typical record of the concentration of sulphur dioxide gas in the atmosphere.

If the display unit is a chart recorder, a trace such as that shown in FIG. 4 may be produced. However the display unit may be of other suitable type, such as a digital meter.

In order to allow the fresh supply of reagent to settle, both in movement and in temperature, the controller 72 prevents the input to the difference amplifier 66 from the amplifier 64 from increasing in accordance with the conductivity change until time D (FIG. 3); this provides a more clearly defined initial increase in measured conductivity. Typically, a cycle lasts for 1 minute, and time D is eighteen seconds from the beginning of the cycle at time A. A sulphur dioxide concentration of a few parts in $10^8$ is detectable.

Since a zero signal is provided by hold unit 70, it is not necessary for the sulphuric acid concentration in the reagent to be zero at the beginning of the cycle; this gives improved accuracy of measurement and also allows the reagent to be recycled to the reservoir, although an overall concentration in sulphuric acid will eventually be reached at which the whole of the reagent must be replaced. For a continuously-operating atmospheric $SO_2$ monitor using a gas-flow rate of 300 milliliters per minute, replacement may be required after about two weeks.

It may be convenient to provide a built-in calibration system, for example, some means for providing at known intervals a sample of $SO_2$ free air, or a sample containing a known concentration of $SO_2$.

Although the invention has been described with reference to the measurement of sulphur dioxide gas in the atmosphere by variation in electrical conductivity of a reagent, it is not limited to this gas or this method. By provision of a suitable reagent, the concentration of other gases, either in the atmosphere or in enclosed volumes in mixtures with other gases which do not dissolve or react with the reagent, may be measured. Instead of measuring electrical conductivity, an optical property such as photoconductivity may be measured by providing a cell with at least partly transparent walls and using a reagent which changes colour when the gas to be detected is absorbed. For example, the concentration of sulphur dioxide gas in air may be detected by measuring the change in colour of a fuchsin dye formulation, or a very dilute solution of iodine in aqueous starch solution.

We claim:

1. Apparatus for determining the concentration of a component of a gaseous mixture by selective absorption of the component in a liquid absorbent and measurement of a property of the absorbent related to the concentration of the component therein, the apparatus comprising an absorption cell for containing the liquid absorbent; means for bringing a stream of said gaseous mixture into contact with the absorbent; means for flushing the absorbent cell at regular intervals of time with absorbent from a reservoir so as to recharge the cell with absorbent; means for returning the absorbent flushed from the cell to the reservoir; and means for providing a first signal related to said property of the absorbent immediately after flushing the cell, for providing a second signal related to said property immediately before flushing the cell in the next interval of time, and for providing a third signal related to the difference between the second and first signals.

2. Apparatus according to claim 1 in which the means for bringing a stream of the gaseous mixture into contact with the absorbent comprises a jet-forming means arranged to direct a jet of the gaseous mixture on to the surface of the absorbent.

3. Apparatus according to claim 1 in which the property of the absorbent related to the concentration of the component therein is the electrical conductivity.

4. Apparatus according to claim 1 further comprising temperature sensitive means arranged to sense the temperature of the absorbent and to compensate the first and second signals in accordance with the sensed temperature.

5. A method of determining the concentration of a component of a gaseous mixture by selective absorption of the component in a liquid absorbent and measurement of a property of the absorbent related to the concentration of the component therein, comprising bringing a stream of gaseous mixture into contact with a quantity of said absorbent in an absorption cell; flushing the absorption cell with absorbent from a reservoir so as to recharge the cell with absorbent; returning the absorbent flushed from the cell to the reservoir; providing a first signal related to said property of the absorbent immediately after flushing the cell, providing a second signal related to the property immediately before flushing the cell in the next interval of time, and providing a third signal related to the difference between the second and first signals.

* * * * *